(12) United States Patent
Reynolds et al.

(10) Patent No.: US 9,662,457 B2
(45) Date of Patent: May 30, 2017

(54) INJECTION DEVICE

(75) Inventors: David L. Reynolds, Bromont (CA);
Daniel MacDonald, Brossard (CA);
Yan Tremblay, Orford (CA); Julie Trépanier, Sherbrooke (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 761 days.

(21) Appl. No.: 13/261,780

(22) PCT Filed: Jun. 1, 2012

(86) PCT No.: PCT/CA2012/000536
§ 371 (c)(1),
(2), (4) Date: May 8, 2015

(87) PCT Pub. No.: WO2012/167353
PCT Pub. Date: Dec. 13, 2012

(65) Prior Publication Data
US 2015/0238706 A1 Aug. 27, 2015

(30) Foreign Application Priority Data
Jun. 10, 2011 (CA) ...................................... 2742555

(51) Int. Cl.
*A61M 5/32* (2006.01)
*A61M 5/24* (2006.01)
(Continued)

(52) U.S. Cl.
CPC ............ *A61M 5/3294* (2013.01); *A61M 5/19* (2013.01); *A61M 5/2448* (2013.01);
(Continued)

(58) Field of Classification Search
CPC .......... A61M 2005/2414; A61M 5/002; A61M 2005/2013; A61M 2005/206; A61J 1/201; A61J 1/2013; A61J 1/2065; A61J 1/2096
See application file for complete search history.

(56) References Cited

U.S. PATENT DOCUMENTS 3,848,593 A * 11/1974 Baldwin .................. 604/206
5,281,198 A * 1/1994 Haber et al. ................ 604/86
(Continued)

FOREIGN PATENT DOCUMENTS

GB 2447787 A * 9/2008
WO WO 9746203 A1 * 12/1997
(Continued)

*Primary Examiner* — Scott Medway
(74) *Attorney, Agent, or Firm* — Eric Fincham (57) ABSTRACT

An injection device which includes a housing (12), a needle hub (38) slidable within the housing (12), a needle (40) having a distal end piercing tip (42) and a proximal end piercing tip (44), the needle hub (40) being moveable from a first position wherein the distal piercing tip (42) is within the housing to a second position wherein the distal end piercing tip (42) extends outwardly of housing (12), a first spring (23) biasing the needle hub (38) towards the first position, and a cartridge receiving member (48) mounted within the housing, and a plunger rod assembly (166), the plunger rod assembly (166) having a distal interior chamber (102) and a proximal interior chamber (103), the distal interior chamber (102) being designed to receive a cartridge (85) containing a liquid (89), the cartridge having a septum (87) and a plunger (88) to prevent exit of the liquid, and a second needle hub (91) located in the proximal chamber, a second hollow needle (92) mounted in the second needle hub, the second hollow needle having a distal piercing tip (94) and a proximal piercing tip (93), the second hollow
(Continued)

needle being moveable from a first non piercing position to a second position whereby said distal piercing tip (94) will pierce the septum (87).

7 Claims, 7 Drawing Sheets (51) Int. Cl.
    *A61M 5/19*         (2006.01)
    *A61M 5/178*       (2006.01)
    *A61M 5/315*       (2006.01)

(52) U.S. Cl.
    CPC ........ *A61M 5/2466* (2013.01); *A61M 5/3202* (2013.01); *A61M 5/326* (2013.01); *A61M 5/3272* (2013.01); *A61M 5/3293* (2013.01); *A61M 5/3298* (2013.01); *A61M 5/1782* (2013.01); *A61M 5/31511* (2013.01); *A61M 5/3287* (2013.01); *A61M 2005/247* (2013.01); *A61M 2005/2407* (2013.01); *A61M 2005/2414* (2013.01); *A61M 2005/3267* (2013.01); *A61M 2005/3289* (2013.01)

(56) References Cited

U.S. PATENT DOCUMENTS

| | | | | |
|---|---|---|---|---|
| 5,807,323 | A  * | 9/1998 | Kriesel et al. | 604/89 |
| 6,981,963 | B2 * | 1/2006 | Barker et al. | 604/90 |
| 7,297,136 | B2 * | 11/2007 | Wyrick | 604/117 |
| 8,162,917 | B2 * | 4/2012 | Stepovich et al. | 604/415 |
| 8,329,119 | B2 * | 12/2012 | Pearcy et al. | 422/514 |
| 8,414,541 | B2 * | 4/2013 | Spofforth | 604/232 |
| 8,814,823 | B2 * | 8/2014 | Pickhard | 604/89 |
| 8,915,889 | B2 * | 12/2014 | Cox et al. | 604/208 |
| 9,089,649 | B2 * | 7/2015 | Davies et al. | |
| 2005/0033234 | A1* | 2/2005 | Sadowski et al. | 604/140 |
| 2005/0113747 | A1* | 5/2005 | Moir | 604/87 |
| 2006/0079834 | A1* | 4/2006 | Tennican et al. | 604/88 |

FOREIGN PATENT DOCUMENTS

WO      WO 2010075920 A1 *   7/2010
WO      WO 2011060541 A1 *   5/2011

* cited by examiner

INJECTION DEVICE

FIELD OF THE INVENTION

The present invention relates to a medical device and more particularly, relates to an injection device.

BACKGROUND OF THE INVENTION

Injection devices are utilized for administering a drug. There are many known injection devices, the most common of which is a syringe. Known syringes basically comprise a cylindrical tube having a needle mounted at the injection end thereof and a plunger mounted at the other end. Intermediate the needle and the plunger is the constituent to be injected.

Syringes frequently are pre-filled and while this is satisfactory for many medicaments, it is less desirable for other medicaments which must be maintained at a certain temperature. This temperature requirement usually necessitates refrigeration of the pre-filled syringe for storage purposes. As will be appreciated, a great deal of space is utilized for the storage of traditional syringes.

A further problem with traditional syringes is the protection of the person doing the injection. Frequently the medicament being injected can pose a risk for the medical personnel using the syringe. This problem is well known and many different devices or arrangements have been proposed in order to prevent accidents for the person injecting the medicament.

SUMMARY OF THE INVENTION

It is an object of the present invention to provide an injection device which provides protection from accidental pricking of the person doing the injection.

It is a further object of the present injection to provide an injection device which does not need to be refrigerated and which can accept a vial of a medicament and safely inject the same into the patient.

According to one aspect of the present invention, there is provided an injection device comprising a housing, an aperture in a side wall of the housing, a needle hub, a needle mounted in the needle hub, the needle having a distal end piercing tip and a proximal end piercing tip, the needle hub being slidably mounted within the housing, the needle hub being moveable from a first position wherein the distal end piercing tip is within the housing to a second position wherein the distal end piercing tip extends outwardly of the housing, a spring biasing the needle hub towards the first position, a cartridge receiving member mounted within the housing, the cartridge receiving member being accessible through the aperture in the side wall of the housing, a plunger rod assembly including a plunger rod for exerting pressure on the cartridge receiving member to move the cartridge and the needle hub from the first position to the second position, the plunger rod having a distal interior chamber and a proximal interior chamber, the distal interior chamber being designed to receive a cartridge containing a liquid, the cartridge having a septum and a plunger to prevent exit of the liquid, a second needle hub located in the proximal chamber, a second hollow needle mounted in the second needle hub, the second needle having a distal piercing tip and a proximal piercing tip, the second needle being moveable from a first non piercing position to a second position whereby the distal piercing tip will pierce the septum, and a second spring mounted so as to exert pressure on the plunger of the liquid containing cartridge.

The injection device of the present invention will typically be utilized for administering a drug to a patient by qualified medical personnel. However, it will be understood that the scope of the invention is not limited to such an arrangement. In some instances, the patient may self-inject utilizing the device of the present invention. Furthermore, the device can be utilized with any animal requiring injection of the medicament.

As used in this specification, the distal end of an object refers to the end thereof which is closest to the end through which the injection is made while the proximal end of an object is the end closer to the hand of the person administering the injection.

The injection device may be formed of any suitable material, including glass, plastics, metallic material, combinations thereof, et cetera. It suffices to say that those knowledgeable in the art will select the materials most suitable for the manufacture of the device.

The housing functions to contain the various components of the invention and conveniently may be formed of a molded plastic or the like. The housing will also interact with the other components to assist in the motions as will be described in greater detail hereinbelow.

The needle hub is arranged to receive a needle having a distal end piercing tip and a proximal end piercing tip. The distal end piercing tip will be a typical injection piercing tip and is of a relatively small diameter as is known in the art.

The cartridge receiving member, in a preferred embodiment, is formed integrally with the needle hub and naturally is movable therewith.

The cartridge receiving member is further characterized by having a partial wall which will extend partially around the cartridge. The remainder is open to receive the cartridge through an aperture in the housing. However, upon movement of the plunger rod upwardly, the cartridge receiving member is caused to rotate such that the aperture in the housing is covered by the cartridge receiving member partial wall. Furthermore, when in the position wherein access may not be provided to the cartridge, the cartridge receiving member cannot be rotated back to its original position.

The injection device of the present invention is designed to reconstitute the drug which frequently comes in a dry form which must be mixed with a diluent prior to injection. Conveniently, the injection device of the present invention includes an arrangement whereby such reconstitution may be accomplished.

To this end, the plunger rod will include a first distal chamber and a second proximal chamber. Mounted in the first distal chamber will be a cartridge containing a diluent. The cartridge will be of the conventional type including a plunger sealing the open end of the cartridge and a septum at the top of the cartridge.

A second needle hub is mounted in the proximal chamber. A second hollow needle is mounted in the second needle hub. The second hollow needle has a proximal piercing tip and a distal piercing tip with fluid communication being established through the hollow needle. The second needle hub is moveable from a first position which is a non piercing position to a second position wherein the distal piercing tip will pierce the septum of the cartridge. This movement of the second needle hub is caused by insertion of a cartridge containing the dry component and exerting a pressure on the moveable needle hub. This will cause the hollow needle to pierce both the septum of the liquid containing cartridge and a septum of the dry component cartridge to thereby establish fluid communication therebetween.

Once fluid communication is established, the second spring will exert pressure on the plunger of the liquid containing cartridge to force the diluent into the dry component cartridge. The cartridge containing the reconstituted drug may then be inserted in the injection device as previously discussed.

BRIEF DESCRIPTION OF THE DRAWINGS

Having thus generally described the invention, reference will be made to the accompanying drawings illustrating an embodiment thereof, in which.

DETAILED DESCRIPTION OF THE INVENTION

Referring to the drawings in greater detail and by reference characters thereto, there is illustrated in FIGS. 1 to 10 the device of the present invention (generally designated by reference numeral 10) along with a cartridge generally designated by reference numeral 26.

Device 10 has an outer generally cylindrically shaped housing 12. A flange 14 is provided at the proximal end of housing 12 while at the distal end of housing 12 there is provided a cap 16. Cap 16 is screwthreadedly engaged with the distal end of housing 12. It will be noted that there is an aperture or opening 17 in cap 16 to provide for a needle passing therethrough. A slot 15 is formed in an area adjacent flange 14 for reasons discussed hereinbelow.

Figure 11:
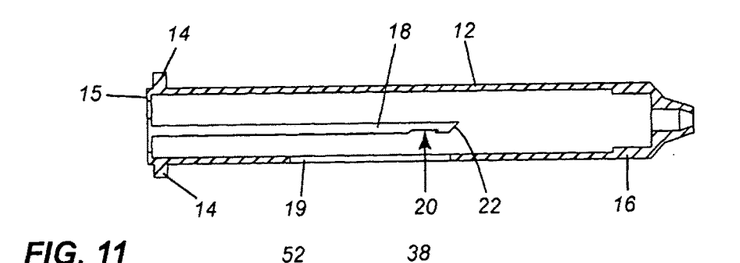
FIG. 11 is a side sectional view of the housing.
Figure 12:
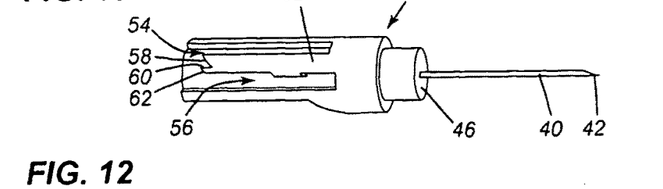
FIG. 12 is a perspective view of the needle hub and cartridge holder.
Figure 13:
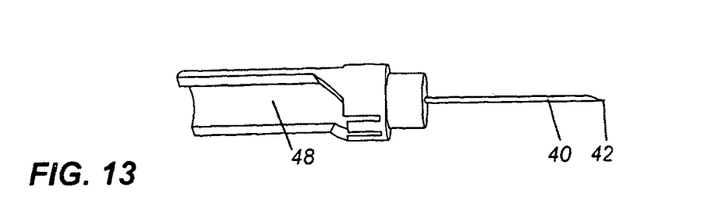
FIG. 13 is a further perspective view of the needle hub and cartridge holder.
Figure 14:
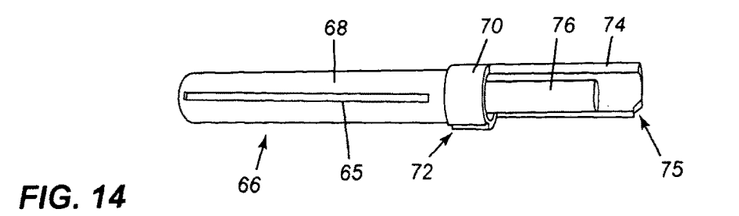
FIG. 14 is a perspective view of the plunger rod assembly.
Figure 15:
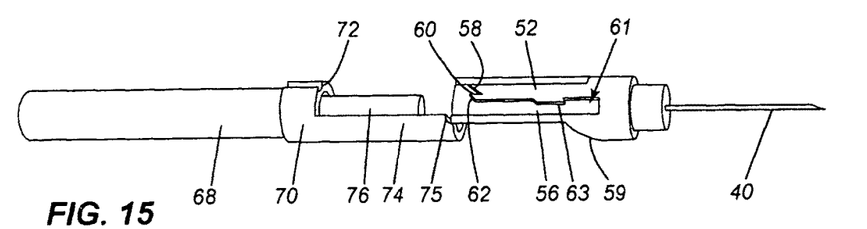
FIG. 15 is a perspective view illustrating the initial engagement of the plunger rod and needle hub.
Figure 16:
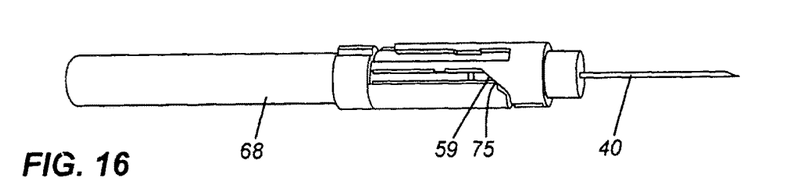
FIG. 16 is a perspective view showing the position of the needle hub and plunger rod after injection.

As may be seen in FIG. 11, there is a longitudinally extending rib 18 formed on the inner surface of housing 12. While rib 18 is shown extending a substantial length of the housing 12, it is only the upper or distal portion which is required in many embodiments. Rib 18 is provided with a recess generally designated by reference numeral 20. Rib 18 also has an angled top wall 22. An opening 19 is provided in housing 12 to permit the insertion of a cartridge as seen in FIGS. 1 to 10.

Cartridge 26 may be a standard cartridge or vial and will contain the medicament to be injected into the patient. Cartridge 26, as is conventional in the art, has a septum 28 and a cap 30 covering septum 28. A plunger 32 is mounted interiorly of the cartridge at the proximal end thereof to prevent loss of medicament 34.

A moveable needle hub 38 is mounted within housing 12 and there is provided a needle 40. Needle 40 includes a distal end piercing tip 42 for injection into the patient and a proximal piercing tip 44 which is arranged to pierce septum 28 of cartridge 26 to provide access to medicament 34.

Needle hub 38 has an upper cylindrical portion 46 and a cartridge receiving member defined by a lower semi-cylindrical wall 48 depending downwardly therefrom. On the exterior of semi-cylindrical wall 48, there is formed a recess 50 which extends partially into wall 48. A raised land portion 52 is located within recess 50 to define a first channel 54 and a second channel 56. A recess 61 is formed in second channel 56 by protrusion 63. At the lower end of raised land portion 52, there is provided a first angled bottom wall 58 which meets a side wall 60 so as to form a small notch. On the opposite side, there is provided a second angled bottom wall 62. A further angled wall section 59 is provided on needle hub 38 proximate an upper portion thereof.

A plunger rod assembly generally designated by reference numeral 66 has a lower cylindrical portion 68 at the top of which there is formed a enlarged portion 70 having a slot 72 formed therein for reasons which will be discussed hereinbelow. A rib 65 is formed on the exterior of lower cylindrical portion 68 for engagement with slot 15.

Plunger rod 66 also includes an upper partial wall 74 which extends about a central pushing rod 76 which is sized to fit within vial 26 to push plunger 32. At an upper corner of upper partial will 74, there is provided a recess 75 having a hook configuration.

Figures 1, 2:
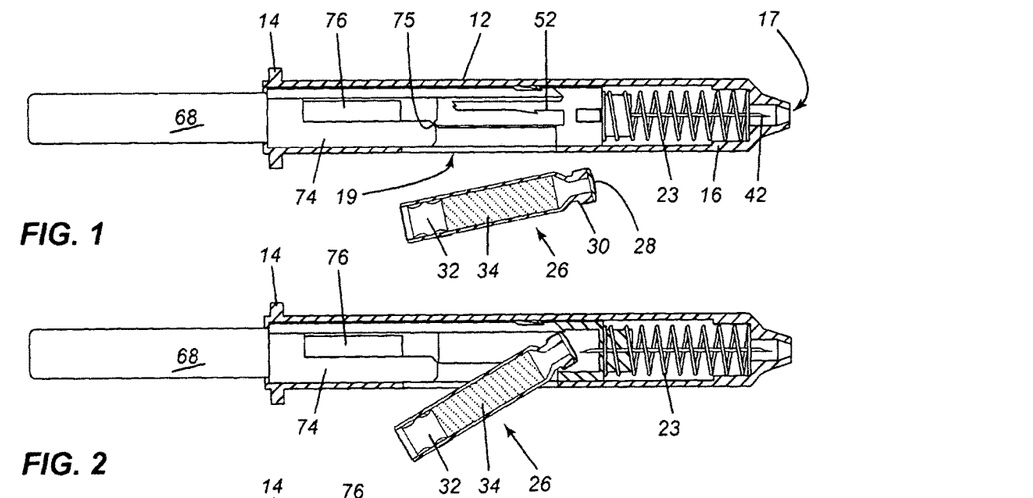
FIG. 1 is a side sectional view illustrating the device and a cartridge.
FIG. 2 is a side sectional view illustrating placement of the cartridge in the device.
Figure 3:
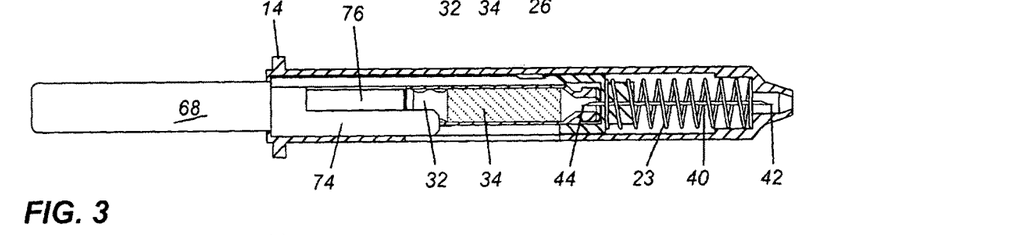
FIG. 3 is a side sectional view illustrating the cartridge in the device with piercing of the septum.
Figure 4:
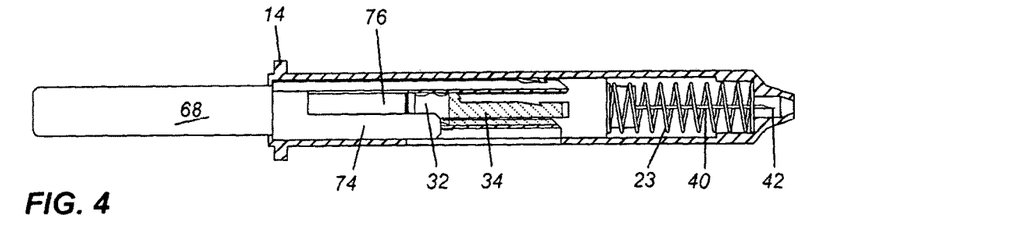
FIG. 4 is a side sectional view illustrating initial movement of the cartridge within the holder.
Figure 5:
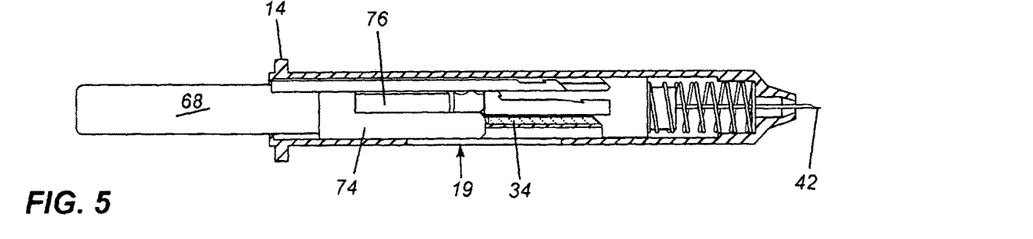
FIG. 5 is a side sectional view illustrating further movement of the cartridge and needle hub.
Figure 6:
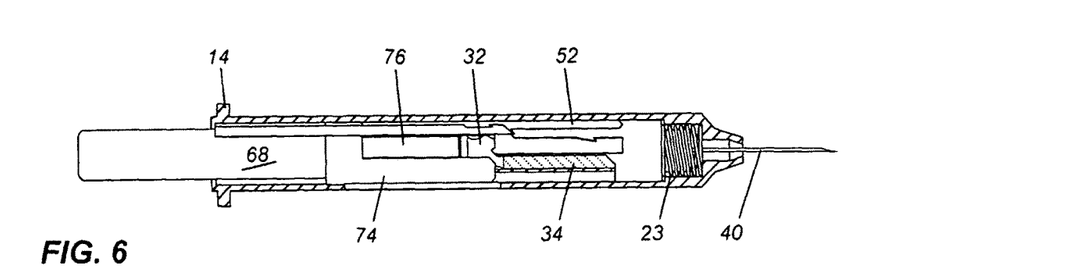
FIG. 6 is a side sectional view illustrating further movement of a plunger rod.
Figure 7:
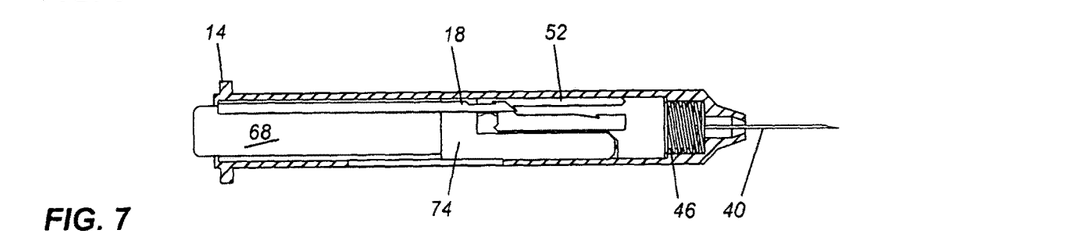
FIGS. 7 and 8 are side sectional views illustrating progression of the movement and injection of the cartridge contents.
Figure 8:
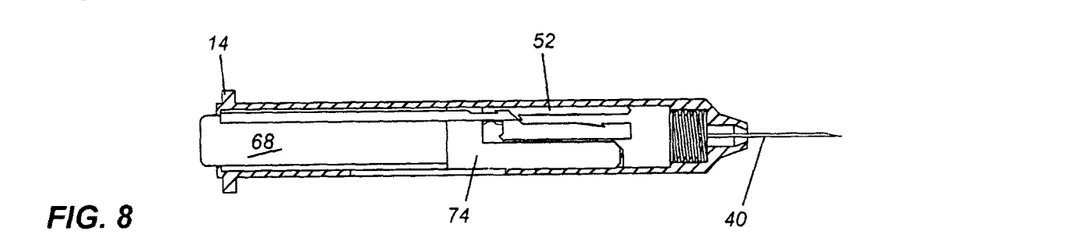
Figure 9:
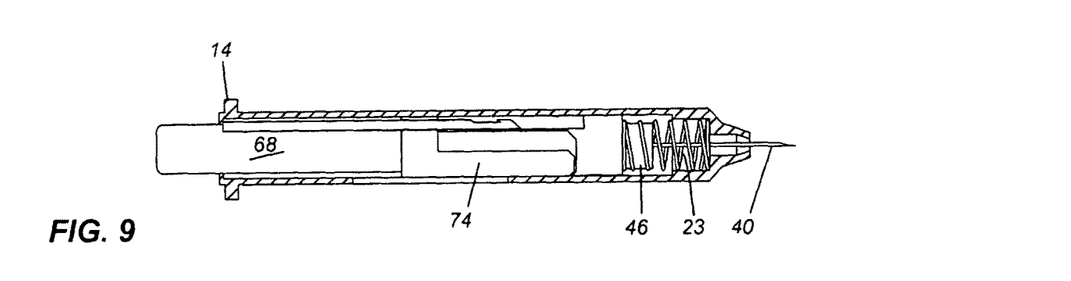
FIG. 9 is a side sectional view illustrating rearward movement of the needle hub, cartridge and cartridge holder.
Figure 10:
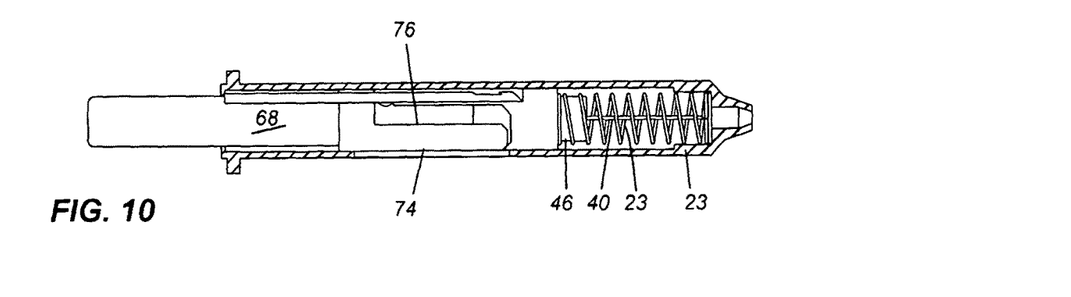
FIG. 10 is a side sectional view illustrating the device after injection and withdrawal of the needle.

Vial 26 is inserted through opening 19 in housing 12 as may be seen in FIGS. 1 and 2. If desired, it can be arranged such that vial 26 has septum 28 pierced by lower piercing end 44 upon insertion. A spring 23 extends about the upper portion of needle 40.

Initially, recess portion 75 engages end wall 62 which is tapered. The hooked nature of recess 75 ensures that the two walls remain in contact for a period of time sufficient for piercing end 44 to pierce septum 28. Continued pressure on plunger rod 66 will cause corners 75 and 71 to disengage and impart a rotational movement to needle hub 38. In turn, this will allow rib 18 to enter first channel 54. Continued pressure on plunger rod 66 will cause corner 75 to contact slanted wall 59. This causes a further rotation of needle hub 38 with respect to housing 12. This further rotation will cause the upper end of rib 18 to enter into channel 56. In so doing, pressure will be exerted until the top of rib 18 enters recess 61. The rib is then in a locked position and needle hub 38 is pushed rearwardly by spring 23.

The continued engagement of the top of rib 18 within recess 61 assures that the needle cannot be exposed as it is locked in place.

A modified device is illustrated in the embodiment of FIGS. 17A to 17G. Where components identical to those of the embodiment of FIGS. 1 to 16 are shown, similar reference numerals in the 100's are employed.

Device 110 has an overall generally cylindrically shaped housing 112. A flange 114 is situated at the proximal end of housing 112 while at the distal end of housing 112 there is provided a cap 116 which is screwthreadably engaged with the distal end of housing 112. As previously shown, there is an opening 117 in cap 116 to allow for a needle to pass therethrough.

The inner surface of housing 112 has a rib (not shown) thereon as in the previously described embodiment. Housing 112 also includes an opening 119 to permit the insertion of a cartridge.

The illustrated arrangement provides a cartridge 80 having a cap 81 and a septum 82. A plunger 83 is provided to retain a dry component 84 within cartridge 80.

A second cartridge 85 is mounted interiorly of plunger rod 166. Cartridge 85 includes a cap 86, a septum 87 and a plunger 88. Diluent 89 is mounted interiorly of cartridge 85. Plunger rod 166 has a distal interior chamber 102 and a proximal interior chamber 103.

Mounted within plunger rod 166 is a second needle hub 91 having needle 92 mounted interiorly thereof. Needle 92 includes a first piercing end 93 and a second piercing end 94. A coil spring 90 is mounted to abut plunger 88.

Figure 17A:
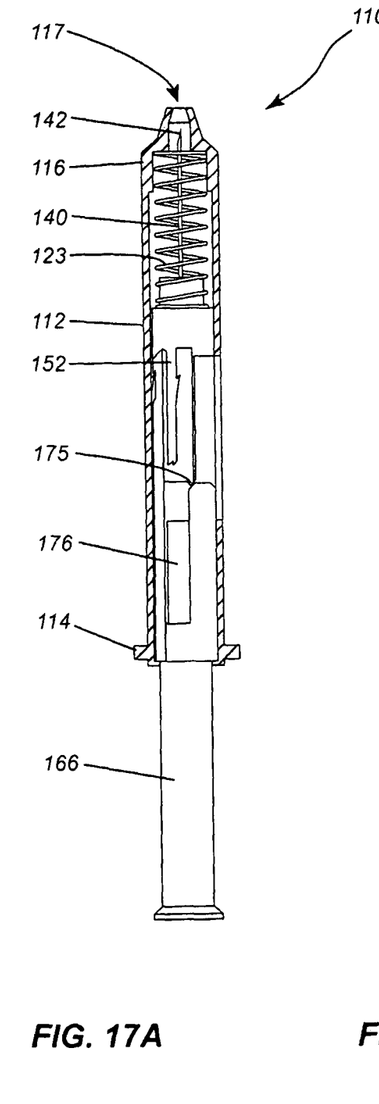
FIGS. 17A to 17G illustrate a modified version of the device.
Figure 17B:
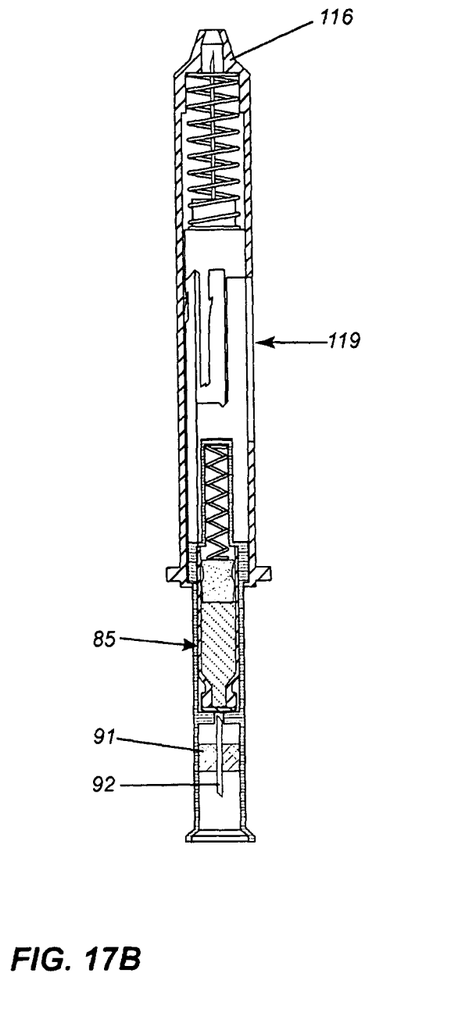
Figure 17C:
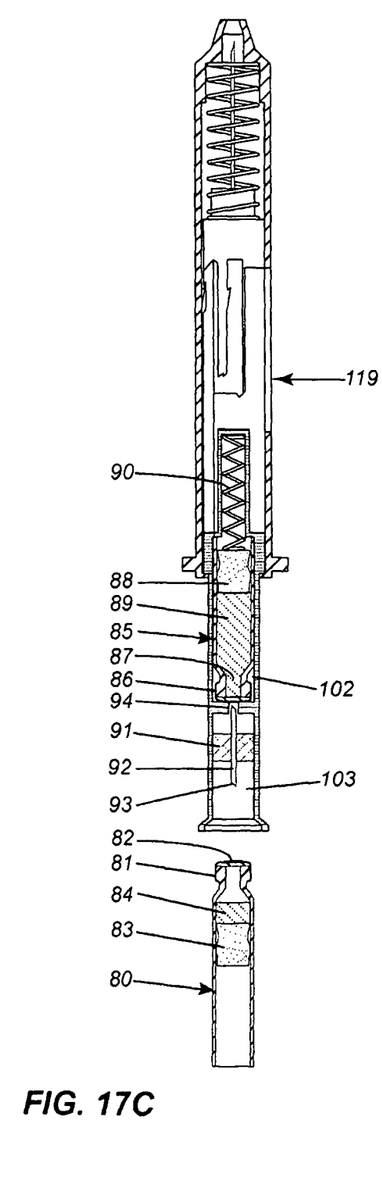
Figure 17D:
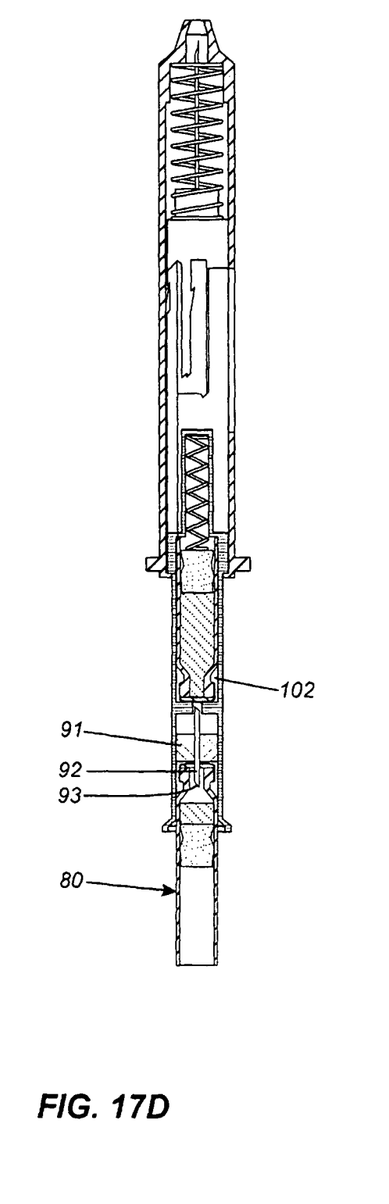
Figure 17E:
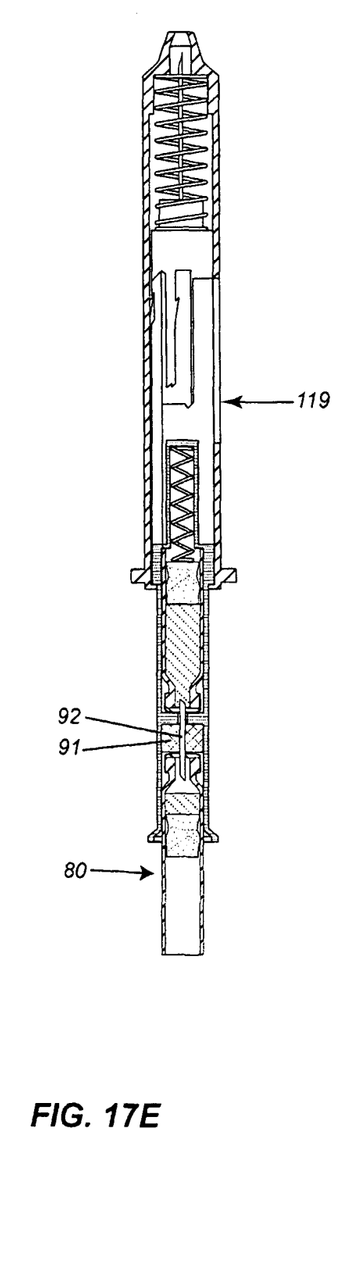
Figure 17F:
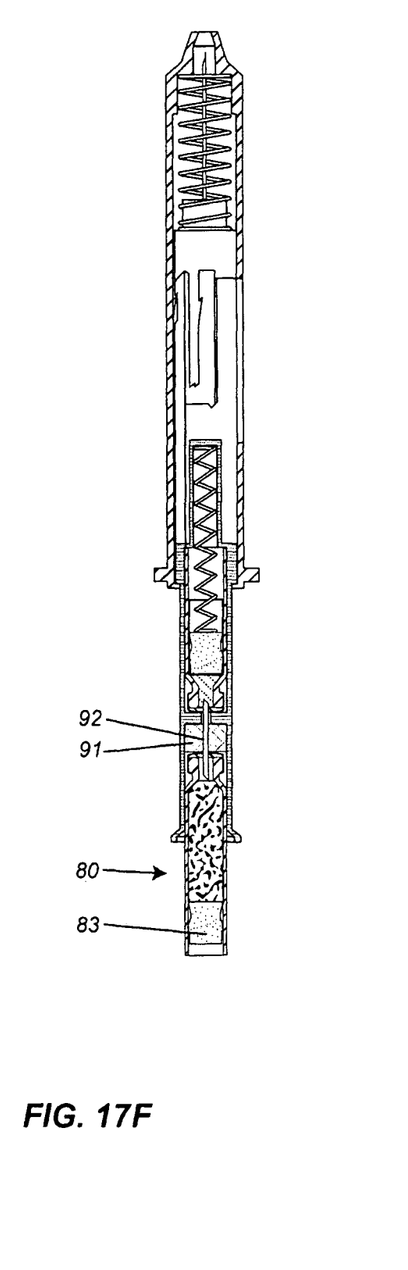
Figure 17G:
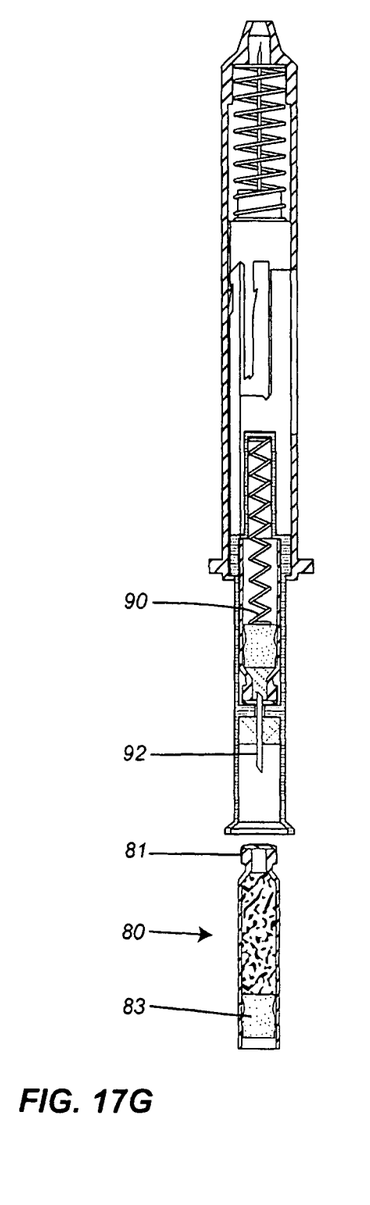

In operation, cartridge 80 containing the dry component is inserted into the interior of plunger rod 66. Proximal piercing end 93 of needle 92 will then puncture septum 82 of cartridge 80 as shown in FIG. 17D. Continued movement of cartridge 80 upwardly will then cause needle hub 91 to move such that distal piercing end 94 pierces septum 87 of cartridge 85 to provide a fluid passage path between the two cartridges as shown in FIG. 17E. Spring 90 will function to push plunger 88 to expel diluent 89 from cartridge 85 into cartridge 80 (FIG. 17F). Cartridge 80 may then be removed and placed interiorly of the body of housing 12 (FIG. 17G) as in the previously described embodiment. The remaining operations will remain identical to the previously described embodiment.

We claim:

1. An injection device comprising:
    a housing (12), an aperture (19) in a side wall of said housing;
    a needle hub (38), a needle (40) mounted in said needle hub (38), said needle (40) having a distal end piercing tip (42) and a proximal end piercing tip (44), said needle hub (38) being slidably mounted within said housing (12), said needle hub (38) being moveable from a first position wherein said distal end piercing tip (42) is within said housing (12) to a second position wherein said distal end piercing tip (42) extends outwardly of said housing (12);
    a spring (22) biasing said needle hub (38) towards said first position;
    a cartridge receiving member (48) mounted within said housing, said cartridge receiving member (48) being accessible through said aperture (19) in said side wall of said housing;
    a plunger rod assembly (166) including a plunger rod for exerting pressure on said cartridge receiving member (48) to move said needle hub (38) from said first position to said second position;
    said plunger rod having a distal interior chamber (102) and a proximal interior chamber (103), said distal interior chamber being designed to receive a cartridge (85) containing a liquid (89), said cartridge having a septum (87) and a plunger (88) to prevent exit of said liquid;
    a second needle hub (91) located in said proximal chamber, a second hollow needle (92) mounted in said second needle hub (91), said second needle having a distal piercing tip (94) and a proximal piercing tip (93), said second hollow needle (92) being moveable from a first non piercing position to a second position whereby said distal piercing tip (94) will pierce said septum (87); and
    a second spring (90) mounted so as to exert pressure on said plunger of said liquid containing cartridge.

2. The injection device of claim 1 further including a second cartridge (80), said second cartridge (80) containing a dry component (84), said second cartridge having a second cartridge septum (81) and a second cartridge plunger (83), said second cartridge (80) being insertable in said proximal chamber (103) to exert pressure on said second needle hub (91) such that said second needle will pierce said septum (86) of said first container and said septum (81) of said second container.

3. The injection device of claim 1 wherein said cartridge receiving member (48) and
    said needle hub (38) are integral.

4. The injection device of claim 3 wherein said plunger rod assembly (66) has a pusher rod (76) and an upper partial wall (74) partially surrounding said pusher wall, said upper partial wall (74) having a length greater than said pusher rod (76).

5. The injection device of claim 4 wherein said upper partial wall (74) has an angled corner (75), said cartridge receiving member (48) having a cartridge receiving member partial wall, said cartridge receiving member partial wall having a tapered corner (62) to engage with said angled corner (75) on said upper partial wall (74) to permit pushing of said cartridge receiving member (48) upwardly.

6. The injection device of claim 5 wherein contact of said upper partial wall (74) and said cartridge receiving member partial wall causes said cartridge receiving member (48) to rotate and thereby cause said cartridge receiving member partial wall to block said opening in said housing to thereby prevent removal of said cartridge therefrom.

7. The injection device of claim 6 wherein said housing has a protrusion on an inner surface thereof, said cartridge receiving member having first and second channels, said second channel having a recess formed therein to engage said protrusion on said inner surface of said housing to prevent further movement of said cartridge receiving member.

* * * * *